(12) United States Patent
Chatterton et al.

(10) Patent No.: US 8,168,609 B2
(45) Date of Patent: May 1, 2012

(54) RNAI-MEDIATED INHIBITION OF RHO KINASE FOR TREATMENT OF OCULAR DISORDERS

(75) Inventors: Jon E. Chatterton, Fort Worth, TX (US); Abbot F. Clark, Arlington, TX (US)

(73) Assignee: Alcon Research, Ltd., Fort Worth, TX (US)

(*) Notice: Subject to any disclaimer, the term of this patent is extended or adjusted under 35 U.S.C. 154(b) by 0 days.

(21) Appl. No.: 12/940,375

(22) Filed: Nov. 5, 2010

(65) Prior Publication Data

US 2011/0245319 A1 Oct. 6, 2011

Related U.S. Application Data

(62) Division of application No. 12/500,239, filed on Jul. 9, 2009, now abandoned, which is a division of application No. 11/641,410, filed on Dec. 19, 2006, now abandoned.

(60) Provisional application No. 60/754,094, filed on Dec. 27, 2005.

(51) Int. Cl.
  *C12N 15/11* (2006.01)
  *C07H 21/02* (2006.01)
(52) U.S. Cl. .................... 514/44 A; 536/24.5
(58) Field of Classification Search .................... None
  See application file for complete search history.

(56) References Cited

U.S. PATENT DOCUMENTS

| | | | |
|---|---|---|---|
| 2004/0115641 A1 | 6/2004 | Cowsert et al. | |
| 2005/0019746 A1 | 1/2005 | Seery et al. | |
| 2005/0222029 A1 | 10/2005 | Bartel et al. | |
| 2005/0255487 A1* | 11/2005 | Khvorova et al. | 435/6 |
| 2007/0031844 A1 | 2/2007 | Khuorova et al. | |

FOREIGN PATENT DOCUMENTS

| | | |
|---|---|---|
| WO | 2004087744 | 10/2004 |
| WO | 2005063976 | 7/2005 |
| WO | 2005085466 | 9/2005 |
| WO | 2005085469 | 9/2005 |
| WO | 2005117938 | 12/2005 |

OTHER PUBLICATIONS

Atsuko, et al.; "The Rho kinases I and II regulate different aspects of myosin II activity"; Aug. 3, 2005; pp. 443-453; vol. 170, No. 3; Journal of Cell Biology.
Brown, et al.; "Target accessibility dictates the potency of human RISC", Nature Structural & Molecular Biology, vol. 12, No. 5, pp. 469-470 (2005).
Campochiaro P.A.; "Potential Applications for RNAi to Probe Pathogenesis and Develop New Treatments for Ocular Disorders", Sep. 29, 2005; pp. 559-562; vol. 13; No. 6; Gene Therapy.

Heale, et al.; "siRNA target site secondary structure predictions using local stable substructures", Nucleic Acids Research, vol. 33, No. 3, pp. e30 (2005).
Honjo, et al. "Effects of Rho-associated Protein Kinase Inhibitor Y-27632 on Intraocular Pressure and Outflow Facility"; Jan. 2001, pp. 137-144; vol. 42, No. 1, Investigative Ophthalmology and Visual Science, Association for Research in Vision.
Jing, et al., "Myristoylated alanine-rich C kinase substrate-mediated neurotensin release via protein kinase c-delta downstream of the Rho/ROK pathway"; Dec. 28, 2004; pp. 8351-8357; vol. 280, No. 9; Journal of Biological Chemistry, American Society of Biolochemical Biologists.
Kim, et al., "Synthetic dsRNA dicer substrates enhance RNAi potency and efficacy"; Nature Biotechnology; 2004; 23:2:222-226.
Masahiro, et al., "Development of Specific Rho-kinase Inhibitors and Their Clinical Application", Sep. 12, 2005; pp. 245-252; vol. 1754; No. 1-2; Biochimica Et Biophysica Acta Dec. 30, 2005.
Orlando, et al; "Rho kinase regulates fragmentation and phagocytosis of apoptotic cells"; Nov. 2, 2005; pp. 5-15; vol. 312; No. 1; Experimental Cell Research.
Pang, et al., "Preliminary characterization of a transformed cell strain derived from human trabecular meshwork"; Curr Eye Res.; 1994; 13:51-6.
Rao, Ponugoti Vasantha, et al., "Expression of dominant negative Rho-binding domain of Rho-kinase in organ cultured human eye anterior segments increases aqueous humor outflow"; Molecular Vision 2005; pp. 288-297, 11, Molvis, World Wide Web.
Rao, P. Vansantha, et al., "Modulation of Aqueous Humor Outflow Facility by the Rho Kinase-Specific Inhibitor Y-27632"; Investigative Ophthalmology & Visual Science, Apr. 2001, vol. 42, No. 5, pp. 1029-1037; Association for Research in Vision and Ophthalmology; Rockville, MD, USA.
Schubert, et al.; "Local RNA target structure influences siRNA efficacy: systematic analysis of intentionally designed binding regions"; J. Mol. Biol., vol. 348, pp. 883-893 (2005).
Vickers, et al.; "Effects of RNA secondary structure on cellular antisense activity", Nucleic Acids Research, vol. 28, No. 6, pp. 1340-1347 (2000).
Waki, M. et al., "Reduction of intraocular pressure by topical administration of an inhibitor of the Rho-associated protein kinase"; Curr Eye Res.; 2005; 22:470-4.
Yoneda, A., et al., "The Rho kinases I and II regulate different aspects of myosin II activity"; J Cell Biology, 2005, 170:443-53.
Zhang & Hua; "Targeted gene silencing by small interfering RNA-based knock-down technology"; Current Pharmaceutical Biotechnology; vol. 5; pp. 1-7 (2004).
Opalinska and Gewirtz; "Nucleic-acid therapeutic: basic principles and recent applications"; Nature Reviews; Drug Discovery; vol. 1; pp. 503-514 (Jul. 2002).
Matveeva, et al.; "Thermodynamic criteria for high hit rate antisense oligonucleotide design"; Nucleic Acids Research; vol. 31; No. 1; pp. 4989-4994 (2003).

(Continued)

*Primary Examiner* — Richard Schnizer
(74) *Attorney, Agent, or Firm* — Jason J. Derry

(57) ABSTRACT

RNA interference is provided for inhibition of Rho kinase mRNA expression for treating patients with ocular disorders, particularly for treating intraocular pressure, ocular hypertension and glaucoma. Rho kinase mRNA targets include mRNA for ROCK1 and ROCK2.

15 Claims, 4 Drawing Sheets

OTHER PUBLICATIONS

Crooke; "Molecular mechanisms of action of antisense drugs"; Biochimica et Biophysica Acta; vol. 1489; pp. 31-44 (1999).

Coburn & Cullen; "siRNAs: a new wave of RNA-based therapeutics"; The Journal of Antimicrobial Chemotherapy; vol. 51; No. 4; pp. 753-756 (2003).

Caplen; "RNAi as a gene therapy approach"; Gene Therapy; Expert Opinion Biol. Ther.; vol. 3; No. 4; pp. 575-586 (2003).

Agrawl and Kandimalla; "Antisense therapeutics: is it as simple as complementary base recognition"; Reviews: Molecular Medicine Today; vol. 6; pp. 72-81 (Feb. 2000).

Agami; "RNAi and related mechanisms and their potential use for therapy"; Biopolymers; Current Opinion in Chemical Biology; vol. 6; pp. 829-834 (2002).

* cited by examiner

SEQUENCE LISTING

```
<160> NUMBER OF SEQ ID NOS: 84

<210> SEQ ID NO 1
<211> LENGTH: 4065
<212> TYPE: DNA
<213> ORGANISM: Homo sapiens

<400> SEQUENCE: 1
atgtcgactg gggacagttt tgagactcga tttgaaaaaa tggacaacct gctgcgggat     60
```

```
cccaaatcgg aagtgaattc ggattgtttg ctggatggat tggatgcttt ggtatatgat    120
ttggattttc ctgccttaag aaaaaacaaa aatattgaca acttttttaag cagatataaa    180 gacacaataa ataaaatcag agatttacga atgaaagctg aagattatga agtagtgaag    240
gtgattggta gaggtgcatt tggagaagtt caattggtaa ggcataaatc caccaggaag    300
gtatatgcta tgaagcttct cagcaaattt gaaatgataa agagatctga ttctgctttt    360
ttctgggaag aaagggacat catggctttt gccaacagtc cttgggttgt tcagcttttt    420
tatgcattcc aagatgatcg ttatctctac atggtgatgg aatacatgcc tggtggagat    480
cttgtaaact aatgagcaa ctatgatgtg cctgaaaaat gggcacgatt ctatactgca    540
gaagtagttc ttgcattgga tgcaatccat tccatgggtt ttattcacag agatgtgaag    600
cctgataaca tgctgctgga taaatctgga catttgaagt tagcagattt tggtacttgt    660
atgaagatga ataaggaagg catggtacga tgtgatacag cggttggaac acctgattat    720
atttcccctg aagtattaaa atcccaaggt ggtgatggtt attatggaag agaatgtgac    780
tggtggtcgg ttggggtatt tttatacgaa atgcttgtag gtgatacacc tttttatgca    840
gattctttgg ttggaactta cagtaaaatt atgaaccata aaaattcact tacctttcct    900
gatgataatg acatatcaaa agaagcaaaa aaccttattt gtgccttcct tactgacagg    960
gaagtgaggt tagggcgaaa tggtgtagaa gaaatcaaac gacatctctt cttcaaaaat    1020
gaccagtggg cttgggaaac gctccgagac actgtagcac cagttgtacc cgatttaagt    1080
agtgacattg atactagtaa ttttgatgac ttggaagaag ataaaggaga ggaagaaaca    1140
ttccctattc ctaaagcttt cgttggcaat caactaccctt tgtaggatt tacatattat    1200 agcaatcgta gatacttatc ttcagcaaat cctaatgata acagaactag ctccaatgca    1260
gataaaagct tgcaggaaag tttgcaaaaa acaatctata agctggaaga acagctgcat    1320
aatgaaatgc agttaaaaga tgaaatggag cagaagtgca gaacctcaaa cataaaacta    1380
gacaagataa tgaaagaatt ggatgaagag ggaaatcaaa gaagaaatct agaatctaca    1440
gtgtctcaga ttgagaagga gaaaatgttg ctacagcata gaattaatga gtaccaaaga    1500
aaagctgaac aggaaaatga gaagagaaga aatgtagaaa atgaagtttc tacattaaag    1560
gatcagttgg aagacttaaa gaaagtcagt cagaattcac agcttgctaa tgagaagctg    1620
tcccagttac aaaagcagct agaagaagcc aatgacttac ttaggacaga atcggacaca    1680
gctgtaagat tgaggaagag tcacacagag atgagcaagt caattagtca gttagagtcc    1740
ctgaacagag agttgcaaga gagaaatcga attttagaga attctaagtc acaaacagac    1800
aaagattatt accagctgca agctatatta gaagctgaac gaagagacag aggtcatgat    1860
tctgagatga ttggagacct tcaagctcga attcatcttt acaagaggg ggtgaagcat    1920 ctcaaacata atctcgaaaa agtggaagga gaaagaaaag aggctcaaga catgcttaat    1980
cactcagaaa aggaaaagaa taatttagag atagatttaa actacaaact taaatcatta    2040
caacaacggt tagaacaaga ggtaaatgaa cacaaagtaa ccaaagctcg tttaactgac    2100
aaacatcaat ctattgaaga ggcaaagtct gtggcaatgt gtgagatgga aaaaagctg    2160 aaagaagaaa gagaagctcg agagaaggct gaaaatcggg ttgttcagat tgagaaacag    2220
tgttccatgc tagacgttga tctgaagcaa tctcagcaga aactagaaca tttgactgga    2280
aataaagaaa ggatggagga tgaagttaag aatctaaccc tgcaactgga gcaggaatca    2340
aataagcggc tgttgttaca aaatgaattg aagactcaag catttgaggc agacaattta    2400
aaaggtttag aaaagcagat gaaacaggaa ataaatactt tattggaagc aaagagatta    2460
```

```
ttagaatttg agttagctca gcttacgaaa cagtatagag gaaatgaagg acagatgcgg    2520
gagctcaaag atcagcttga agctgagcaa tatttctcga cactttataa aacccaggta    2580
aaggaactta agaagaaat tgaagaaaaa aacagagaaa atttaaagaa aatacaggaa    2640
ctacaaaatg aaaagaaac tcttgctact cagttggatc tagcagaaac aaaagctgag    2700
tctgagcagt tggcgcgagg ccttctggaa gaacagtatt ttgaattgac gcaagaaagc    2760
aagaaagctg cttcaagaaa tagacaagag attacagata aagatcacac tgttagtcgg    2820
cttgaagaag caaacagcat gctaaccaaa gatattgaaa tattaagaag agagaatgaa    2880
gagctaacag agaaaatgaa gaaggcagag gaagaatata aactggagaa ggaggaggag    2940
atcagtaatc ttaaggctgc ctttgaaaag aatatcaaca ctgaacgaac ccttaaaaca    3000
caggctgtta acaaattggc agaaataatg aatcgaaaag attttaaaat tgatagaaag    3060
aaagctaata cacaagattt gagaaagaaa gaaaggaaa atcgaaagct gcaactggaa    3120
ctcaaccaag aaagagagaa attcaaccag atggtagtga acatcagaa ggaactgaat    3180
gacatgcaag cgcaattggt agaagaatgt gcacatagga atgagcttca gatgcagttg    3240
gccagcaaag agagtgatat tgagcaattg cgtgctaaac ttttggacct ctcggattct    3300
acaagtgttg ctagttttcc tagtgctgat gaaactgatg gtaacctccc agagtcaaga    3360
attgaaggtt ggcttttcagt accaaataga ggaaatatca aacgatatgg ctggaagaaa    3420
cagtatgttg tggtaagcag caaaaaaatt ttgttctata atgacgaaca agataaggag    3480
caatccaatc catctatggt attggacata gataaactgt ttcacgttag acctgtaacc    3540
caaggagatg tgtatagagc tgaaactgaa gaaattccta aaatattcca gatactatat    3600
gcaaatgaag gtgaatgtag aaaagatgta gagatggaac cagtacaaca agctgaaaaa    3660
actaatttcc aaaatcacaa aggccatgag tttattccta cactctacca ctttcctgcc    3720
aattgtgatg cctgtgccaa acctctctgg catgttttta gccacccccc tgccctagag    3780
tgtcgaagat gccatgttaa gtgccacaga gatcacttag ataagaaaga ggacttaatt    3840
tgtccatgta aagtaagtta tgatgtaaca tcagcaagag atatgctgct gttagcatgt    3900
tctcaggatg aacaaaaaaa atgggtaact catttagtaa agaaaatccc taagaatcca    3960
ccatctggtt tgttcgtgc ttcccctcga acgctttcta caagatccac tgcaaatcag    4020
tctttccgga aagtggtcaa aaatacatct ggaaaaacta gttaa    4065
```

<210> SEQ ID NO 2
<211> LENGTH: 6401
<212> TYPE: DNA
<213> ORGANISM: Homo sapiens

<400> SEQUENCE: 2

```
caaggcggcc ggcggcgacc atggcagcgg gccggcggcg gccgtagtgg cccaggcctg      60
ggcttcagcc tcccggggcc ccagagggcg gggcggtccg ggccgcggcg gtggcggcgc     120
cacttccctg ctcccgcccg aggactcctg cgggcactcg ctgaggacca gcggaccggc     180
ggcgcgaatc tgactgaggg gcgggacgc cgtctgttcc ccgccgctcc cggcagggcc     240
gggccgggct gggccgggct gggccggggcg ggccctgggg agcagccccc aggcggggga    300
ccgccttgga gacccgaagc cggagctaga ggcaggcggt gggcccgggt ggagtcccgg     360
ccggagctgg tggttcgggg gcggtgctag gccccgaggc tgcgggacct gagcgcgagg     420
agcctgagtg cgggtccagc ggtgtgcggca tgagccggcc cccgccgacg gggaaaatgc     480
ccggcgcccc cgagaccgcg ccggggggacg gggcaggcgc gagccgccag aggaagctgg     540
```

```
aggcgctgat ccgagaccct cgctccccca tcaacgtgga gagcttgctg gatggcttaa      600
attccttggt ccttgattta gattttcctg ctttgaggaa aaacaagaac atagataatt      660
tcttaaatag atatgagaaa attgtgaaaa aaatcagagg tctacagatg aaggcagaag      720
actatgatgt tgtaaaagtt attggaagag gtgcttttgg tgaagtgcag ttggttcgtc      780
acaaggcatc gcagaaggtt tatgctatga agcttcttag taagtttgaa atgataaaaa      840
gatcagattc tgccttttt tgggaagaaa gagatattat ggcctttgcc aatagcccct      900
gggtggttca gcttttttat gcctttcaag atgataggta tctgtacatg gtaatggagt      960
acatgcctgg tggagacctt gtaaacctta tgagtaatta tgatgtgcct gaaaatgggg     1020
ccaaatttta cactgctgaa gttgttcttg ctctggatgc aatacactcc atgggtttaa     1080
tacacagaga tgtgaagcct gacaacatgc tcttggataa acatggacat ctaaaattag     1140
cagattttgg cacgtgtatg aagatggatg aaacaggcat ggtacattgt gatacagcag     1200
ttggaacacc ggattatata tcacctgagg ttctgaaatc acaaggggt gatggtttct      1260 atgggcgaga atgtgattgg tggtctgtag gtgttttcct ttatgagatg ctagtggggg     1320
atactccatt ttatgcggat tcacttgtag gaacatatag caaaattatg gatcataaga     1380
attcactgtg tttccctgaa gatgcagaaa tttccaaaca tgcaaagaat ctcatctgtg     1440
ctttcttaac agatagggag gtacgacttg ggagaaatgg ggtggaagaa atcagacagc     1500
atccttcctt taagaatgat cagtggcatt gggataacat aagagaaacg gcagctcctg     1560
tagtacctga actcagcagt gacatagaca gcagcaattt cgatgacatt gaagatgaca     1620
aaggagatgt agaaaccttc ccaattccta agcttttgt tggaaatcag ctgcctttca      1680
tcggatttac ctactataga gaaaatttat tattaagtga ctctccatct tgtagagaaa     1740
ctgattccat acaatcaagg aaaatgaag aaagtcaaga gattcagaaa aaactgtata      1800
cattagaaga acatcttagc aatgagatgc aagccaaaga ggaactggaa cagaagtgca     1860
aatctgttaa tactcgccta gaaaaaacag caaaggagct agaagaggag attaccttac     1920
ggaaaagtgt ggaatcagca ttaagacagt tagaaagaga aaaggcgctt cttcagcaca     1980
aaaatgcaga atatcagagg aaagctgatc atgaagcaga caaaaaacga aatttggaaa     2040
atgatgttaa cagcttaaaa gatcaacttg aagatttgaa aaaagaaat caaaactctc      2100 aaatatccac tgagaaagtg aatcaactcc agagacaact ggatgaaacc aatgctttac     2160
tgcgaacaga gtctgatact gcagcccggt taaggaaaac ccaggcagaa agttcaaaac     2220
agattcagca gctggaatct aacaatagag atctacaaga taaaaactgc ctgctggaga     2280
ctgccaagtt aaaacttgaa aaggaattta tcaatcttca gtcagctcta gaatctgaaa     2340
ggagggatcg aacccatgga tcagagataa ttaatgattt acaaggtaga atatgtggcc     2400
tagaagaaga tttaaagaac ggcaaaatct tactagcgaa agtagaactg gagaagagac     2460
aacttcagga gagatttact gatttggaaa aggaaaaaag caacatggaa atagatatga     2520
cataccaact aaaagttata cagcagagcc tagaacaaga agaagctgaa cataaggcca     2580
caaaggcacg actagcagat aaaaataaga tctatgagtc catcgaagaa gccaaatcag     2640
aagccatgaa agaaatggag aagaagctct tggaggaaag aactttaaaa cagaaagtgg     2700
agaacctatt gctagaagct gagaaaagat gttctctatt agactgtgac tcaaacagt      2760 cacagcagaa aataaatgag ctccttaaac agaaagatgt gctaaatgag gatgttagaa     2820
acctgacatt aaaaatagag caagaaactc agagcgctg ccttacacaa aatgacctga      2880
agatgcaaac acaacaggtt aacacactaa aaatgtcaga aaagcagtta aagcaagaaa     2940
```

```
ataaccatct catggaaatg aaaatgaact tggaaaaaca aaatgctgaa cttcgaaaag    3000
aacgtcagga tgcagatggg caaatgaaag agctccagga tcagctcgaa gcagaacagt    3060
atttctcaac cctttataaa acacaagtta gggagcttaa agaagaatgt gaagaaaaga    3120
ccaaacttgg taaagaattg cagcagaaga acaggaatt acaggatgaa cgggactctt     3180
tggctgccca actggagatc accttgacca aagcagattc tgagcaactg gctcgttcaa    3240
ttgctgaaga acaatattct gatttggaaa agagaagat catgaaagag ctggagatca     3300
aagagatgat ggctagacac aaacaggaac ttacggaaaa agatgctaca attgcttctc    3360
ttgaggaaac taataggaca ctaactagtg atgttgccaa tcttgcaaat gagaaagaag    3420
aattaaataa caaattgaaa gatgttcaag agcaactgtc aagattgaaa gatgaagaaa    3480
taagcgcagc agctattaaa gcacagtttg agaagcagct attaacagaa agaacactca    3540
aaactcaagc tgtgaataag ttggctgaga tcatgaatcg aaaagaacct gtcaagcgtg    3600
gtaatgacac agatgtgcgg agaaaagaga aggagaatag aaagctacat atggagctta    3660
aatctgaacg tgagaaattg acccagcaga tgatcaagta tcagaaagaa ctgaatgaaa    3720
tgcaggcaca aatagctgaa gagagccaga ttcgaattga actgcagatg acattggaca    3780
gtaaagacag tgacattgag cagctgcggt cacaactcca agccttgcat attggtctgg    3840
atagttccag tataggcagt ggaccagggg atgctgaggc agatgatggg tttccagaat    3900
caagattaga aggatggctt tcattgcctg tacgaaacaa cactaagaaa tttggatggg    3960
ttaaaaagta tgtgattgta agcagtaaga agattctttt ctatgacagt gaacaagata    4020
aagaacaatc caatccttac atggttttag atatagacaa gttatttcat gtccgaccag    4080
ttacacagac agatgtgtat agagcagatg ctaaagaaat tccaaggata ttccagattc    4140
tgtatgccaa tgaaggagaa agtaagaagg aacaagaatt tccagtggag ccagttggag    4200
aaaaatctaa ttatatttgc cacaagggac atgagtttat tcctactctt tatcatttcc    4260
caaccaactg tgaggcttgt atgaagcccc tgtggcacat gtttaagcct cctcctgctt    4320
tggagtgccg ccgttgccat attaagtgtc ataaagatca tatggacaaa aggaggaga    4380 ttatagcacc ttgcaaagta tattatgata tttcaacggc aaagaatctg ttattactag    4440
caaattctac agaagagcag cagaagtggg ttagtcggtt ggtgaaaaag atacctaaaa    4500
agcccccagc tccagaccct tttgcccgat catctcctag aacttcaatg aagatacagc    4560
aaaaccagtc tattagacgg ccaagtcgac agcttgcccc aaacaaacct agctaactgc    4620
cttctatgaa agcagtcatt attcaaggtg atcgtattct tccagtgaaa acaagactga    4680
aatatgatgg cccaaaattt attaaaaagc tatattttcc tgagagactg atacatacac    4740
tcatacatat atgtgttccc cttttccctg taatataaat tacaaatctg gctcctttg     4800 aagcaacagg ttgaaccaac aatgattggt tgatagacta aggatatatg caactcttcc    4860
agacttttcc ataaagctct ctcggcagtc gctcacacta caatgcacac aaggattgag    4920
aagagttaaa ggctaaagaa aacatctttt ctagcttcaa cagagaggtt tcaccagcac    4980
atttaccaga agaatctggg aatggattcc actacagtga tattgactgc atctttaaga    5040
agtgaccatt atactgtgta tatatatata aacacacaca catatatata tatatatata    5100
gtactctaat actgcaagaa ggtttttttaa acttcccact ttattttta tacacattaa    5160 tcagatatca ttacttgctg cagttgcaac tatgcacttg tataaagcca taatgttgga    5220
gtttatatca ctcattcctg tgtacctgat ggaagttgca tgttcatgtt taagcagtta    5280
ctgtaacaag aagtttaaag ttaattatat cagtttccta atgcttcatg ataggcaact    5340
```

```
ttacccattt tgaatgcctt aatttaattt ttttcaaagt ctcagccctg tctgtattaa    5400
aaaacaaaaa aagcgtttac cagctcttag gatgtaaact agctttgtgg aagataaatc    5460
gtgcactatt tttacacata aatagttata tcaatgtcag cctattttga ttaacaaatg    5520
tttttaaagt attattggtt atagaaacaa taatggatgg tgttggaact aatatatcct    5580
tgatgtctgt ctattattca ttcaactctt tttacagacc tcagtattag tctgtgacta    5640
caaaatattt tatttgcttt aaatttgctg gctaccctag atgtgttttt attcctggta    5700
aagacatttg tgattacatt ttcacactta agattcaaaa ttttccccaa atataaagaa    5760
aactaagaca gactgtagat gcattttaaa tatttaaata tgatcctcag acatgcagct    5820
gtgtgtggca gtattttagt accgggttaa gaaaactggc aactgggaag aagtggcctc    5880
aaaggcactt aatttgattt ttattttta aatgctgtca aagttacagt ttacgcagga    5940
cattcttgcc gtattctcat gatcccagat aagtgtgtgt tttatactgc aacaatatgc    6000
agcaatggta agcgtaaagt tttttttttg tttttgtttt tttttatatt atgaagtctt    6060
ttaacagtct ctctttatat aaatacacag agtttggtat gatatttaaa tacatcatct    6120
ggccaggcat ggtggcttac gcctgtaatc ctagcacttt gggaggccaa gacgggcgga    6180
tcacctgagg tgaggagttc aagaccagcc tgcccaacat agtgaaactc cgtctctacc    6240
aatatacaaa aattagccgg gcatgatggt ggtggcctgt aatcccagct acttgggagg    6300
ctgagacagg agaatcgctt gaacccagga gacggtggtt gcagtgagcg aagatcgagc    6360
cactgcactc cagcctgggc agctgaacaa gactccgtct c                      6401
```

<210> SEQ ID NO 3
<211> LENGTH: 19
<212> TYPE: DNA
<213> ORGANISM: Artificial
<220> FEATURE:
<223> OTHER INFORMATION: Target Sequence

<400> SEQUENCE: 3
ataacatgct gctggataa                                                  19

<210> SEQ ID NO 4
<211> LENGTH: 21
<212> TYPE: DNA
<213> ORGANISM: Artificial
<220> FEATURE:
<223> OTHER INFORMATION: Sense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 4
auaacaugcu gcuggauaan n                                               21

<210> SEQ ID NO 5
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:

```
<221> NAME/KEY: misc_feature
<222> LOCATION: (20)..(21)
<223> OTHER INFORMATION: any, A, T/U, C, G

<400> SEQUENCE: 5
uuauccagca gcauguuaun n                                              21

<210> SEQ ID NO 6
<211> LENGTH: 21
<212> TYPE: RNA
<213> ORGANISM: Artificial
<220> FEATURE:
<223> OTHER INFORMATION: Sense Strand

<400> SEQUENCE: 6
auaacaugcu gcuggauaau u                                              21

<210> SEQ ID NO 7
<211> LENGTH: 21
<212> TYPE: RNA
<213> ORGANISM: Artificial
<220> FEATURE:
<223> OTHER INFORMATION: Antisense Strand

<400> SEQUENCE: 7
uuauccagca gcauguuauu u                                              21

<210> SEQ ID NO 8
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: ribonucleotides

<400> SEQUENCE: 8
auaacaugcu gcuggauaan nnnnnnnuua uccagcagca uguuauuu                 48

<210> SEQ ID NO 9
<211> LENGTH: 19
<212> TYPE: DNA
<213> ORGANISM: Artificial
<220> FEATURE:
<223> OTHER INFORMATION: Target Sequence

<400> SEQUENCE: 9
gtacttgtat gaagatgaa                                                 19

<210> SEQ ID NO 10
<211> LENGTH: 19
<212> TYPE: DNA
<213> ORGANISM: Artificial
<220> FEATURE:
<223> OTHER INFORMATION: Target Sequence

<400> SEQUENCE: 10
gtatgaagat gaataagga                                                 19
```

```
<210> SEQ ID NO 11
<211> LENGTH: 19
<212> TYPE: DNA
<213> ORGANISM: Artificial
<220> FEATURE:
<223> OTHER INFORMATION: Target Sequence

<400> SEQUENCE: 11
tagctccaat gcagataaa                                              19

<210> SEQ ID NO 12
<211> LENGTH: 19
<212> TYPE: DNA
<213> ORGANISM: Artificial
<220> FEATURE:
<223> OTHER INFORMATION: Target Sequence

<400> SEQUENCE: 12
atcagttgga agacttaaa                                              19

<210> SEQ ID NO 13
<211> LENGTH: 19
<212> TYPE: DNA
<213> ORGANISM: Artificial
<220> FEATURE:
<223> OTHER INFORMATION: Target Sequence

<400> SEQUENCE: 13
gaccttcaag ctcgaatta                                              19

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
gaacatttga ctggaaata                                              19

<210> SEQ ID NO 15
<211> LENGTH: 19
<212> TYPE: DNA
<213> ORGANISM: Artificial
<220> FEATURE:
<223> OTHER INFORMATION: Target Sequence

<400> SEQUENCE: 15
tagctcagct tacgaaaca                                              19

<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
acgaaacagt atagaggaa                                              19

<210> SEQ ID NO 17
<211> LENGTH: 19
<212> TYPE: DNA
<213> ORGANISM: Artificial
<220> FEATURE:
<223> OTHER INFORMATION: Target Sequence
```

<400> SEQUENCE: 17
tttgaattga cgcaagaaa                                                19

<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
cactgttagt cggcttgaa                                                19

<210> SEQ ID NO 19
<211> LENGTH: 19
<212> TYPE: DNA
<213> ORGANISM: Artificial
<220> FEATURE:
<223> OTHER INFORMATION: Target Sequence

<400> SEQUENCE: 19
acagcatgct aaccaaaga                                                19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
gttaacaaat tggcagaaa                                                19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
accagatggt agtgaaaca                                                19

<210> SEQ ID NO 22
<211> LENGTH: 19
<212> TYPE: DNA
<213> ORGANISM: Artificial
<220> FEATURE:
<223> OTHER INFORMATION: Target Sequence

<400> SEQUENCE: 22
gtagaagaat gtgcacata                                                19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
gcaaagagag tgatattga                                                19

<210> SEQ ID NO 24
<211> LENGTH: 19
<212> TYPE: DNA

```
<213> ORGANISM: Artificial
<220> FEATURE:
<223> OTHER INFORMATION: Target Sequence

<400> SEQUENCE: 24
gtaccaaata gaggaaata                                                  19

<210> SEQ ID NO 25
<211> LENGTH: 19
<212> TYPE: DNA
<213> ORGANISM: Artificial
<220> FEATURE:
<223> OTHER INFORMATION: Target Sequence

<400> SEQUENCE: 25
gttctataat gacgaacaa                                                  19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
gataaactgt ttcacgtta                                                  19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
taaactgttt cacgttaga                                                  19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
gtttcacgtt agacctgta                                                  19

<210> SEQ ID NO 29
<211> LENGTH: 19
<212> TYPE: DNA
<213> ORGANISM: Artificial
<220> FEATURE:
<223> OTHER INFORMATION: Target Sequence

<400> SEQUENCE: 29
tgtcgaagat gccatgtta                                                  19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
gtcgaagatg ccatgttaa                                                  19
```

```
<210> SEQ ID NO 31
<211> LENGTH: 19
<212> TYPE: DNA
<213> ORGANISM: Artificial
<220> FEATURE:
<223> OTHER INFORMATION: Target Sequence

<400> SEQUENCE: 31
acaacatgct cttggataa                                              19

<210> SEQ ID NO 32
<211> LENGTH: 19
<212> TYPE: DNA
<213> ORGANISM: Artificial
<220> FEATURE:
<223> OTHER INFORMATION: Target Sequence

<400> SEQUENCE: 32
tgttaatact cgcctagaa                                              19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
gaaagctgat catgaagca                                              19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
cagctggaat ctaacaata                                              19

<210> SEQ ID NO 35
<211> LENGTH: 19
<212> TYPE: DNA
<213> ORGANISM: Artificial
<220> FEATURE:
<223> OTHER INFORMATION: Target Sequence

<400> SEQUENCE: 35
gatatgacat accaactaa                                              19

<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
aggcacgact agcagataa                                              19

<210> SEQ ID NO 37
<211> LENGTH: 19
<212> TYPE: DNA
<213> ORGANISM: Artificial
<220> FEATURE:
<223> OTHER INFORMATION: Target Sequence
```

```
<400> SEQUENCE: 37
attagactgt gacctcaaa                                               19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
gatgatggct agacacaaa                                               19

<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
ctaaagaaat tccaaggat                                               19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
tcgtattctt ccagtgaaa                                               19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41
ttgcaactat gcacttgta                                               19

<210> SEQ ID NO 42
<211> LENGTH: 19
<212> TYPE: DNA
<213> ORGANISM: Artificial
<220> FEATURE:
<223> OTHER INFORMATION: Target Sequence

<400> SEQUENCE: 42
caactatgca cttgtataa                                               19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
gttgcatgtt catgtttaa                                               19

<210> SEQ ID NO 44
<211> LENGTH: 19
<212> TYPE: DNA
```

```
<213> ORGANISM: Artificial
<220> FEATURE:
<223> OTHER INFORMATION: Target Sequence

<400> SEQUENCE: 44
ttcctaatgc ttcatgata                                                    19

<210> SEQ ID NO 45
<211> LENGTH: 19
<212> TYPE: DNA
<213> ORGANISM: Artificial
<220> FEATURE:
<223> OTHER INFORMATION: Target Sequence

<400> SEQUENCE: 45
ctagctttgt ggaagataa                                                    19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
gaagataaat cgtgcacta                                                    19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
ccttgatgtc tgtctatta                                                    19

<210> SEQ ID NO 48
<211> LENGTH: 19
<212> TYPE: DNA
<213> ORGANISM: Artificial
<220> FEATURE:
<223> OTHER INFORMATION: Target Sequence

<400> SEQUENCE: 48
cttgatgtct gtctattat                                                    19

<210> SEQ ID NO 49
<211> LENGTH: 19
<212> TYPE: DNA
<213> ORGANISM: Artificial
<220> FEATURE:
<223> OTHER INFORMATION: Target Sequence

<400> SEQUENCE: 49
tttacagacc tcagtatta                                                    19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
tattagtctg tgactacaa                                                    19
```

```
<210> SEQ ID NO 51
<211> LENGTH: 19
<212> TYPE: DNA
<213> ORGANISM: Artificial
<220> FEATURE:
<223> OTHER INFORMATION: Target Sequence

<400> SEQUENCE: 51
taaatatgat cctcagaca                                                    19

<210> SEQ ID NO 52
<211> LENGTH: 19
<212> TYPE: DNA
<213> ORGANISM: Artificial
<220> FEATURE:
<223> OTHER INFORMATION: Target Sequence

<400> SEQUENCE: 52
cagcaatggt aagcgtaaa                                                    19

<210> SEQ ID NO 53
<211> LENGTH: 19
<212> TYPE: DNA
<213> ORGANISM: Artificial
<220> FEATURE:
<223> OTHER INFORMATION: Target Sequence

<400> SEQUENCE: 53
ctccgtctct accaatata                                                    19

<210> SEQ ID NO 54
<211> LENGTH: 19
<212> TYPE: DNA
<213> ORGANISM: Artificial
<220> FEATURE:
<223> OTHER INFORMATION: Target Sequence

<400> SEQUENCE: 54
tgatggtggt ggcctgtaa                                                    19

<210> SEQ ID NO 55
<211> LENGTH: 19
<212> TYPE: DNA
<213> ORGANISM: Artificial
<220> FEATURE:
<223> OTHER INFORMATION: Target Sequence

<400> SEQUENCE: 55
cttgctggat ggcttaaat                                                    19

<210> SEQ ID NO 56
<211> LENGTH: 19
<212> TYPE: DNA
<213> ORGANISM: Artificial
<220> FEATURE:
<223> OTHER INFORMATION: Target Sequence

<400> SEQUENCE: 56
ggattcactt gtaggaaca                                                    19

<210> SEQ ID NO 57
<211> LENGTH: 19
<212> TYPE: DNA
<213> ORGANISM: Artificial
<220> FEATURE:
<223> OTHER INFORMATION: Target Sequence
```

```
<400> SEQUENCE: 57
tcatcggatt tacctacta                                                  19

<210> SEQ ID NO 58
<211> LENGTH: 19
<212> TYPE: DNA
<213> ORGANISM: Artificial
<220> FEATURE:
<223> OTHER INFORMATION: Target Sequence

<400> SEQUENCE: 58
taaatgagct ccttaaaca                                                  19

<210> SEQ ID NO 59
<211> LENGTH: 19
<212> TYPE: DNA
<213> ORGANISM: Artificial
<220> FEATURE:
<223> OTHER INFORMATION: Target Sequence

<400> SEQUENCE: 59
gttagaaacc tgacattaa                                                  19

<210> SEQ ID NO 60
<211> LENGTH: 19
<212> TYPE: DNA
<213> ORGANISM: Artificial
<220> FEATURE:
<223> OTHER INFORMATION: Target Sequence

<400> SEQUENCE: 60
ataaccatct catggaaat                                                  19

<210> SEQ ID NO 61
<211> LENGTH: 19
<212> TYPE: DNA
<213> ORGANISM: Artificial
<220> FEATURE:
<223> OTHER INFORMATION: Target Sequence

<400> SEQUENCE: 61
tctcttgagg aaactaata                                                  19

<210> SEQ ID NO 62
<211> LENGTH: 19
<212> TYPE: DNA
<213> ORGANISM: Artificial
<220> FEATURE:
<223> OTHER INFORMATION: Target Sequence

<400> SEQUENCE: 62
caatcttgca aatgagaaa                                                  19

<210> SEQ ID NO 63
<211> LENGTH: 19
<212> TYPE: DNA
<213> ORGANISM: Artificial
<220> FEATURE:
<223> OTHER INFORMATION: Target Sequence

<400> SEQUENCE: 63
taagcgcagc agctattaa                                                  19

<210> SEQ ID NO 64
<211> LENGTH: 19
<212> TYPE: DNA
```

-continued

<213> ORGANISM: Artificial
<220> FEATURE:
<223> OTHER INFORMATION: Target Sequence

<400> SEQUENCE: 64
gagaatagaa agctacata                                                19

<210> SEQ ID NO 65
<211> LENGTH: 19
<212> TYPE: DNA
<213> ORGANISM: Artificial
<220> FEATURE:
<223> OTHER INFORMATION: Target Sequence

<400> SEQUENCE: 65
gctacatatg gagcttaaa                                                19

<210> SEQ ID NO 66
<211> LENGTH: 19
<212> TYPE: DNA
<213> ORGANISM: Artificial
<220> FEATURE:
<223> OTHER INFORMATION: Target Sequence

<400> SEQUENCE: 66
ctacatatgg agcttaaat                                                19

<210> SEQ ID NO 67
<211> LENGTH: 19
<212> TYPE: DNA
<213> ORGANISM: Artificial
<220> FEATURE:
<223> OTHER INFORMATION: Target Sequence

<400> SEQUENCE: 67
gatgacattg gacagtaaa                                                19

<210> SEQ ID NO 68
<211> LENGTH: 19
<212> TYPE: DNA
<213> ORGANISM: Artificial
<220> FEATURE:
<223> OTHER INFORMATION: Target Sequence

<400> SEQUENCE: 68
tctggatagt tccagtata                                                19

<210> SEQ ID NO 69
<211> LENGTH: 19
<212> TYPE: DNA
<213> ORGANISM: Artificial
<220> FEATURE:
<223> OTHER INFORMATION: Target Sequence

<400> SEQUENCE: 69
gaacaatcca atccttaca                                                19

<210> SEQ ID NO 70
<211> LENGTH: 19
<212> TYPE: DNA
<213> ORGANISM: Artificial
<220> FEATURE:
<223> OTHER INFORMATION: Target Sequence

<400> SEQUENCE: 70
gtatagagca gatgctaaa                                                19

```
<210> SEQ ID NO 71
<211> LENGTH: 19
<212> TYPE: DNA
<213> ORGANISM: Artificial
<220> FEATURE:
<223> OTHER INFORMATION: Target Sequence

<400> SEQUENCE: 71
ataaagccat aatgttgga                                              19

<210> SEQ ID NO 72
<211> LENGTH: 19
<212> TYPE: DNA
<213> ORGANISM: Artificial
<220> FEATURE:
<223> OTHER INFORMATION: Target Sequence

<400> SEQUENCE: 72
tagctttgtg gaagataaa                                              19

<210> SEQ ID NO 73
<211> LENGTH: 19
<212> TYPE: DNA
<213> ORGANISM: Artificial
<220> FEATURE:
<223> OTHER INFORMATION: Target Sequence

<400> SEQUENCE: 73
aacgacatct cttcttcaa                                              19

<210> SEQ ID NO 74
<211> LENGTH: 19
<212> TYPE: DNA
<213> ORGANISM: Artificial
<220> FEATURE:
<223> OTHER INFORMATION: Target Sequence

<400> SEQUENCE: 74
gaagaaacat tccctattc                                              19

<210> SEQ ID NO 75
<211> LENGTH: 19
<212> TYPE: DNA
<213> ORGANISM: Artificial
<220> FEATURE:
<223> OTHER INFORMATION: Target Sequence

<400> SEQUENCE: 75
tagcaatcgt agatactta                                              19

<210> SEQ ID NO 76
<211> LENGTH: 19
<212> TYPE: DNA
<213> ORGANISM: Artificial
<220> FEATURE:
<223> OTHER INFORMATION: Target Sequence

<400> SEQUENCE: 76
gccaatgact tacttagga                                              19

<210> SEQ ID NO 77
<211> LENGTH: 19
<212> TYPE: DNA
<213> ORGANISM: Artificial
<220> FEATURE:
<223> OTHER INFORMATION: Target Sequence
```

```
<400> SEQUENCE: 77
ggacacagct gtaagattg                                              19

<210> SEQ ID NO 78
<211> LENGTH: 19
<212> TYPE: DNA
<213> ORGANISM: Artificial
<220> FEATURE:
<223> OTHER INFORMATION: Target Sequence

<400> SEQUENCE: 78
gagatgagca agtcaatta                                              19

<210> SEQ ID NO 79
<211> LENGTH: 19
<212> TYPE: DNA
<213> ORGANISM: Artificial
<220> FEATURE:
<223> OTHER INFORMATION: Target Sequence

<400> SEQUENCE: 79
gtaaccaaag ctcgtttaa                                              19

<210> SEQ ID NO 80
<211> LENGTH: 19
<212> TYPE: RNA
<213> ORGANISM: Artificial
<220> FEATURE:
<223> OTHER INFORMATION: Sense Strand

<400> SEQUENCE: 80
auaacaugcu gcuggauaa                                              19

<210> SEQ ID NO 81
<211> LENGTH: 19
<212> TYPE: RNA
<213> ORGANISM: Artificial
<220> FEATURE:
<223> OTHER INFORMATION: Antisense Strand

<400> SEQUENCE: 81
uuauccagca gcauguuau                                              19

<210> SEQ ID NO 82
<211> LENGTH: 25
<212> TYPE: DNA
<213> ORGANISM: Artificial
<220> FEATURE:
<223> OTHER INFORMATION: Sense Strand

<400> SEQUENCE: 82
ataacatgct gctggataaa tctgg                                       25

<210> SEQ ID NO 83
<211> LENGTH: 25
<212> TYPE: RNA
<213> ORGANISM: Artificial
<220> FEATURE:
<223> OTHER INFORMATION: Sense Strand

<400> SEQUENCE: 83
auaacaugcu gcuggauaaa ucugg                                       25

<210> SEQ ID NO 84
<211> LENGTH: 27
<212> TYPE: RNA
```

-continued

```
<213> ORGANISM: Artificial
<220> FEATURE:
<223> OTHER INFORMATION: Antisense Strand

<400> SEQUENCE: 84
ccagauuuau ccagcagcau guuauuu                                       27
```

RNAI-MEDIATED INHIBITION OF RHO KINASE FOR TREATMENT OF OCULAR DISORDERS

CROSS-REFERENCE TO RELATED APPLICATION

The present application is a divisional of U.S. patent application Ser. No. 12/500,239, filed Jul. 9, 2009, which claims priority to Ser. No. 11/641,410 filed Dec. 19, 2006, which claims benefit to U.S. Provisional Patent Application Ser. No. 60/754,094 filed Dec. 27, 2005.

FIELD OF THE INVENTION

The present invention relates to the field of interfering RNA compositions for inhibition of expression of Rho kinase mRNA targets in ocular disorders, particularly for reducing intraocular pressure in the treatment of ocular hypertension and glaucoma.

BACKGROUND OF THE INVENTION

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the optic nerve head (ONH). One of the main risk factors for the development of glaucoma is the presence of ocular hypertension (OHT), i.e., elevated intraocular pressure (IOP). An adequate IOP is needed to maintain the shape of the eye and to provide a pressure gradient to allow for the flow of aqueous humor to the avascular cornea and lens. IOP levels also may be involved in the pathogenesis of normal tension glaucoma (NTG), as evidenced by patients benefiting from IOP lowering medications. Once adjustments for central corneal thickness are made to IOP readings in NTG patients, many of these patients may be found to be ocular hypertensive.

The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous ONH. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

Primary glaucomas result from disturbances in the flow of intraocular fluid that has an anatomical or physiological basis. Secondary glaucomas occur as a result of injury or trauma to the eye or a preexisting disease. Primary open angle glaucoma (POAG), also known as chronic or simple glaucoma, represents the majority of all primary glaucomas. POAG is characterized by the degeneration of the trabecular meshwork, resulting in abnormally high resistance to fluid drainage from the eye. A consequence of such resistance is an increase in the IOP that is required to drive the fluid normally produced by the eye across the increased resistance.

Rho-associated, coiled-coil containing protein kinases, also known as Rho kinases or ROCKs, are effectors of the Rho family of small GTP-binding proteins (Rho GTPases). The Rho GTPase signaling pathway appears to play a role in regulating aqueous humor outflow, for example, by altering the cytoskeletal organization of trabecular meshwork (TM) and/or ciliary muscle (CM) cells. Small molecule inhibitors of Rho kinase cause reversible changes in TM cell morphology and cytoskeletal organization, decrease contractility of isolated CM tissue, and increase aqueous humor outflow facility in organ culture (Waki M. et al., *Curr Eye Res.* 22:470-4 (2001); Honjo M. et al., *Invest Ophthalmol Vis Sci.* 42:137-44 (2001); Rao P V. et al., *Mol Vis.* 11:288-97 (2005); Rao P V. et al., *Invest Ophthalmol Vis Sci.* 42:1029-37 (2001)). Similar effects are generated by expression of dominant negative Rho-binding domains. However, treatment with small molecule inhibitors of Rho kinase also causes vasodilation and conjunctival hyperemia. In addition, the efficacy of small molecule-based therapies is relatively short-lived requiring repeated dosing during each day and, in some cases, the efficacy decreases with time.

In view of the importance of ocular hypertension in glaucoma and the side effects of prior methods of treatment, it would be desirable to have an improved method of treating ocular hypertension.

SUMMARY OF THE INVENTION

The present invention is directed to interfering RNAs that silence Rho kinase mRNA expression, thus lowering intraocular pressure in patients with ocular hypertension or glaucoma or at risk of developing hypertension or glaucoma. Rho kinase targets include ROCK1 (also known as ROCKI, ROKIβ, or p160ROCK) and ROCK2 (also known as ROCKII or ROKα). The interfering RNAs of the invention are useful for treating patients with ocular hypertension or glaucoma such as normal tension glaucoma and open angle glaucoma.

An embodiment of the present invention provides a method of attenuating expression of a Rho kinase mRNA in a subject. The method comprises administering to the subject a composition comprising an effective amount of interfering RNA having a length of 19 to 49 nucleotides and a pharmaceutically acceptable carrier. In one embodiment, administration is to the eye of the subject for attenuating expression of an ocular hypertension target in a human.

In one embodiment of the invention, the interfering RNA comprises a sense nucleotide strand, an antisense nucleotide strand and a region of at least near-perfect contiguous complementarity of at least 19 nucleotides. Further, the antisense strand hybridizes under physiological conditions to a portion of an mRNA corresponding to SEQ ID NO:1 or SEQ ID NO:2 which are sense cDNA sequences encoding ROCK1 and ROCK2, respectively (GenBank accession no. NM_005406, and NM_004850, respectively). The antisense strand has a region of at least near-perfect contiguous complementarity of at least 19 nucleotides with the hybridizing portion of mRNA corresponding to SEQ ID NO:1 or SEQ ID NO:2, respectively. The administration of such a composition attenuates the expression of Rho kinase in the subject.

In one embodiment of the invention, an interfering RNA is designed to target an mRNA corresponding to SEQ ID NO:1 comprising nucleotide 605, 653, 659, 1248, 1562, 1876, 2266, 2474, 2485, 2740, 2808, 2834, 3007, 3146, 3199, 3245, 3379, 3453, 3511, 3513, 3519, 3781, 3782, 998, 1132, 1200, 1648, 1674, 1708, or 2077. In another embodiment of the invention, an interfering RNA is designed to target an mRNA corresponding to SEQ ID NO:2 comprising nucleotide 1102, 1865, 2000, 2229, 2514, 2584, 2738, 3305, 4111, 4652, 5184, 5187, 5255, 5315, 5439, 5450, 5578, 5579, 5611, 5625, 5795, 6000, 6228, 6264, 584, 1337, 1678, 2773, 2814, 2941, 3357, 3398, 3481, 3633, 3644, 3645, 3767, 3836, 4023, 4097, 5202, or 5440.

The present invention further provides for administering a second interfering RNA to a subject in addition to a first interfering RNA. The method comprises administering to the subject a second interfering RNA having a length of 19 to 49 nucleotides and comprising a sense nucleotide strand, an antisense nucleotide strand, and a region of at least near-perfect complementarity of at least 19 nucleotides; wherein the antisense strand of the second interfering RNA hybridizes under physiological conditions to a second portion of mRNA corresponding to SEQ ID NO:1 or SEQ ID NO:2 and the antisense strand has a region of at least near-perfect contiguous complementarity of at least 19 nucleotides with the second hybridizing portion of mRNA corresponding to SEQ ID NO:1 or SEQ ID NO:2, respectively. The second interfering RNA may target the same mRNA as the first interfering RNA or may target a different mRNA. Further, a third, fourth, or fifth, etc. interfering RNA may be administered in a similar manner.

Another embodiment of the invention is a method of attenuating expression of Rho kinase in a subject comprising administering to the subject a composition comprising an effective amount of single-stranded interfering RNA having a length of 19 to 49 nucleotides and a pharmaceutically acceptable carrier.

For attenuating expression of ROCK1, the single-stranded interfering RNA hybridizes under physiological conditions to a portion of mRNA corresponding to SEQ ID NO:1 comprising nucleotide 605, 653, 659, 1248, 1562, 1876, 2266, 2474, 2485, 2740, 2808, 2834, 3007, 3146, 3199, 3245, 3379, 3453, 3511, 3513, 3519, 3781, 3782, 998, 1132, 1200, 1648, 1674, 1708, or 2077, and the interfering RNA has a region of at least near-perfect complementarity of at least 19 nucleotides with the hybridizing portion of mRNA corresponding to SEQ ID NO:1. Expression of ROCK1 is thereby attenuated.

For attenuating expression of ROCK2, the single-stranded interfering RNA hybridizes under physiological conditions to a portion of mRNA corresponding to SEQ ID NO:2 comprising nucleotide 1102, 1865, 2000, 2229, 2514, 2584, 2738, 3305, 4111, 4652, 5184, 5187, 5255, 5315, 5439, 5450, 5578, 5579, 5611, 5625, 5795, 6000, 6228, 6264, 584, 1337, 1678, 2773, 2814, 2941, 3357, 3398, 3481, 3633, 3644, 3645, 3767, 3836, 4023, 4097, 5202, or 5440 and the interfering RNA has a region of at least near-perfect contiguous complementarity of at least 19 nucleotides with the hybridizing portion of mRNA corresponding to SEQ ID NO:2. Expression of ROCK2 is thereby attenuated.

A further embodiment of the invention is a method of treating ocular hypertension or glaucoma in a subject in need thereof. The method comprises administering to the eye of the subject a composition comprising an effective amount of interfering RNA having a length of 19 to 49 nucleotides and a pharmaceutically acceptable carrier, the interfering RNA comprising a sense nucleotide strand, an antisense nucleotide strand, and a region of at least near-perfect contiguous complementarity of at least 19 nucleotides. The antisense strand hybridizes under physiological conditions to a portion of mRNA corresponding to SEQ ID NO:1 or SEQ ID NO: 2 and has a region of at least near-perfect contiguous complementarity of at least 19 nucleotides with the hybridizing portion of mRNA corresponding to SEQ ID NO:1 or SEQ ID NO:2, respectively. The ocular hypertension or glaucoma is treated thereby.

Another embodiment of the invention is a method of treating ocular hypertension or glaucoma in a subject in need thereof, the method comprising administering to an eye of the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of an mRNA corresponding to any one of SEQ ID NO:3 and SEQ ID NO:9-SEQ ID NO:79, wherein the ocular hypertension or glaucoma is treated thereby.

Another embodiment of the invention is a method of attenuating expression of a Rho kinase target mRNA in a subject, comprising administering to the subject a composition comprising an effective amount of interfering RNA having a length of 19 to 49 nucleotides and a pharmaceutically acceptable carrier, where the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:3 and SEQ ID NO:9-SEQ ID NO:79 as follows.

When the Rho kinase target mRNA is ROCK1 mRNA, the interfering RNA comprises a region of at least 13 contiguous nucleotides having at least 90% sequence complementarity to, or at least 90% sequence identity with, the penultimate 13 nucleotides of the 3' end of an mRNA corresponding to SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:73, SEQ ID NO:74, SEQ ID NO:75, SEQ ID NO:76, SEQ ID NO:77, SEQ ID NO:78, or SEQ ID NO:79.

When the Rho kinase target mRNA is ROCK2 mRNA, the interfering RNA comprises a region of at least 13 contiguous nucleotides having at least 90% sequence complementarity to, or at least 90% sequence identity with, the penultimate 13 nucleotides of the 3' end of an mRNA corresponding to SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, or SEQ ID NO:72.

In a further embodiment of the present invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence of the sequence identifier. In yet another embodiment of the invention, the region of contiguous nucleotides is a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to the target sequence identified by the sequence identifier.

A further embodiment of the invention is a method of treating ocular hypertension in a subject in need thereof, the method comprising administering to the subject a composition comprising a double stranded siRNA molecule that down regulates expression of a ROCK1 or ROCK2 gene via RNA interference, wherein each strand of the siRNA molecule is independently about 19 to about 27 nucleotides in length; and one strand of the siRNA molecule comprises a nucleotide sequence having substantial complementarity to an mRNA corresponding to the ROCK1 or ROCK2 gene, respectively, so that the siRNA molecule directs cleavage of the mRNA via RNA interference.

A composition comprising interfering RNA having a length of 19 to 49 nucleotides and having a nucleotide sequence of any one of SEQ ID NO:3, and SEQ ID NO:9-SEQ ID NO:79, or a complement thereof, and a pharmaceutically acceptable carrier is an embodiment of the present invention. In one embodiment, the interfering RNA is isolated. The term "isolated" means that the interfering RNA is free of its total natural mileau.

Another embodiment of the invention is a composition comprising a double stranded siRNA molecule that down regulates expression of a ROCK1 or ROCK2 gene via RNA interference, wherein each strand of the siRNA molecule is independently about 19 to about 27 nucleotides in length; and one strand of the siRNA molecule comprises a nucleotide sequence has substantial complementarity to an mRNA corresponding to the ROCK1 or ROCK2 gene, respectively, so that the siRNA molecule directs cleavage of the mRNA via RNA interference.

The present invention provides an advantage over small molecule inhibitors of Rho kinase since an undesirable side effect of current small molecule therapies, e.g., hyperemia, can be dissociated from the desirable effect of lowering intraocular pressure.

Use of any of the embodiments as described herein in the preparation of a medicament for attenuating expression of ROCK1 or ROCK2 mRNA is also an embodiment of the present invention.

DETAILED DESCRIPTION OF THE INVENTION

Figure 1:
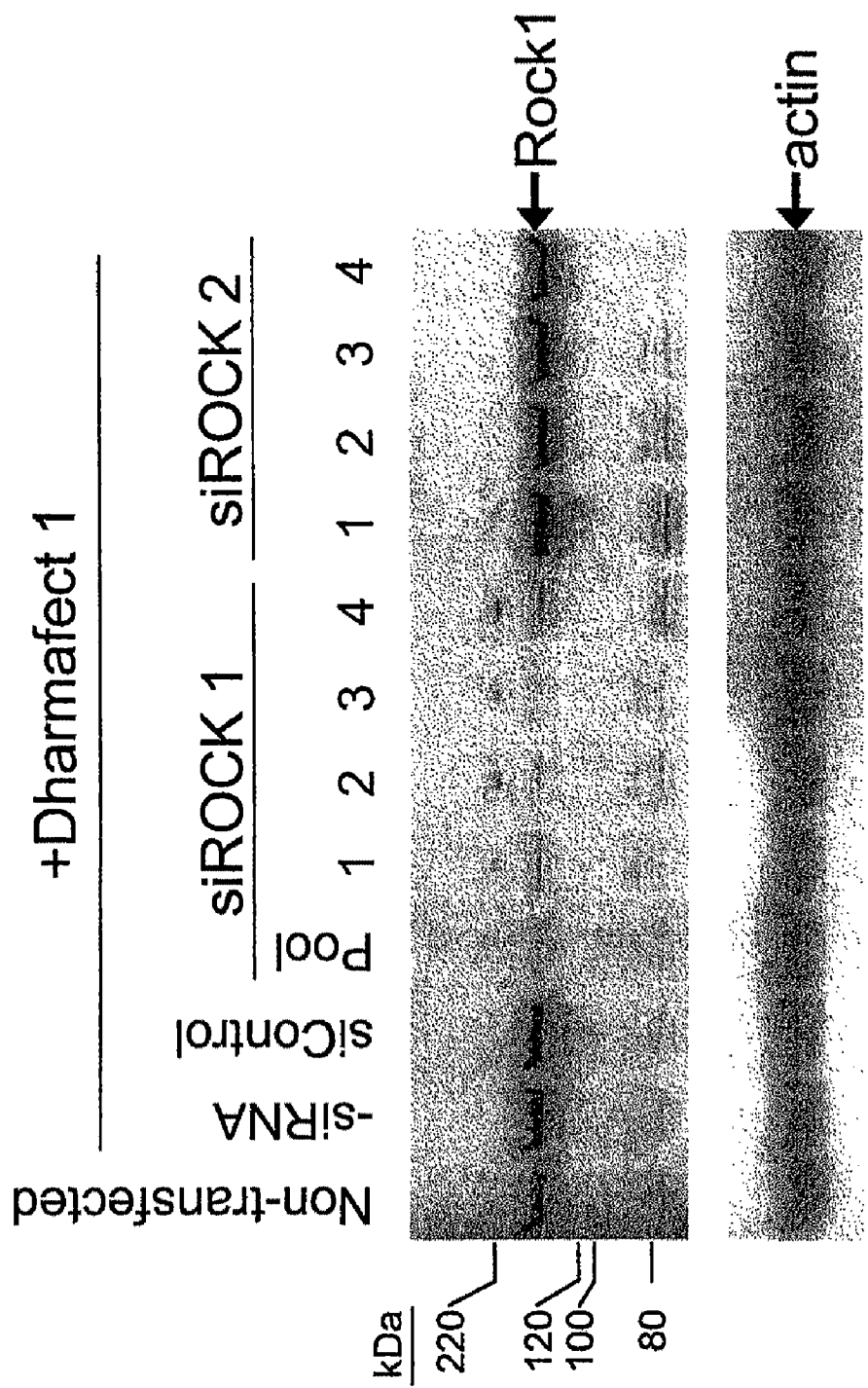
FIG. 1 provides a ROCK1 western blot of GTM-3 cells transfected with ROCK1 siRNAs #1, #2, #3, and #4; ROCK2 siRNAs #1, #2, #3, and #4; a ROCK1 siRNA pool; a non-targeting control siRNA; and a buffer control (-siRNA). The siRNAs were at a concentration of 100 nM. The arrows indicate the positions of the 160-kDa ROCK1 protein and 42-kDa actin protein bands.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of Rho kinase (ROCK) mRNA, thus lowering intraocular pressure in patients with glaucoma. There are two Rho kinase isoforms: ROCK1 (also known as ROCKI, ROKIβ or p160ROCK) and ROCK2 (also known as ROCKII or ROKα). According to the present invention, interfering RNAs as set forth herein provided exogenously or expressed endogenously are particularly effective at silencing ROCK mRNA.

Small molecule inhibitors of ROCK cause reversible changes in trabecular meshwork cell morphology and cytoskeletal organization, decrease contractility of isolated ciliary muscle tissue, and increase aqueous humor outflow facility in organ culture. Similar effects are generated by expression of dominant negative Rho-binding domains. Treatment with small molecule inhibitors of ROCK lowers IOP, however, such treatment also appears to cause hyperemia. The small molecule inhibitors of ROCK examined to date inhibit multiple kinases in addition to ROCK1 and ROCK2. Use of interfering RNAs of the present invention having specificity for ROCK1 or ROCK2 mRNA is expected to dissociate the desirable IOP-lowering effect of treatment from the undesirable hyperemia effect of treatment.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for ROCK1. The mRNA sequence is identical to the DNA sense strand sequence with the "T" bases replaced with "U" bases. Therefore, the mRNA sequence of ROCK1 is known from SEQ ID NO:1 and the mRNA sequence of ROCK2 is known from SEQ ID NO:2.

Rho kinase mRNA (ROCK1 and ROCK2): Rho-associated, coiled-coil containing protein kinases, also known as Rho kinases or simply ROCKs, are effectors of the Rho family of small GTP-binding proteins (Rho GTPases). The Rho GTPase signaling pathway appears to play a role in regulating aqueous humor outflow, for example, by altering the cytoskeletal organization of trabecular meshwork (TM) and/or ciliary muscle (CM) cells.

ROCKs are serine/threonine protein kinases that are activated by GTP-bound Rho. ROCK activation leads to the phosphorylation of several substrates involved in actin filament assembly and cell contractility including myosin light chain, myosin light chain phosphatase, LIM kinase, adducin, ERM, for example. Thus, ROCKs regulate a wide variety of cellular processes including stress-fiber formation, contraction, adhesion, migration, phagocytosis, apoptosis, and cytokinesis. Two ROCK isoforms are ROCK1 (also known as ROCKI, ROKIβ, or p160ROCK) and ROCK2 (also known as ROCKII or ROKα). The two isoforms are highly similar, particularly in their kinase domains (92% identity at the amino acid level), however, they exhibit differences in tissue distribution and intracellular localization suggesting that they may have distinct, non-redundant functions. Both ROCK1 and ROCK2 are expressed in the human eye anterior segment.

The GenBank database of the National Center for Biotechnology Information at ncbi.nlm.nih.gov provides the DNA sequence for ROCK1 as accession no. NM_005406, provided in the "Sequence Listing" as SEQ ID NO:1. SEQ ID NO:1 provides the sense strand sequence of DNA that corresponds to the mRNA encoding ROCK1 (with the exception of "T" bases for "U" bases). The coding sequence for ROCK1 is from nucleotides 1-4065.

Equivalents of the above cited ROCK1 mRNA sequence are alternative splice forms, allelic forms, isozymes, or a cognate thereof. A cognate is a ROCK1 mRNA from another mammalian species that is homologous to SEQ ID NO:1 (an ortholog).

The GenBank database provides the DNA sequence for ROCK2 as accession no. NM_004850, provided in the "Sequence Listing" as SEQ ID NO:2. SEQ ID NO:2 provides the sense strand sequence of DNA that corresponds to the mRNA encoding ROCK2 (with the exception of "T" bases for "U" bases). The coding sequence for ROCK2 is from nucleotides 450-4616.

Equivalents of the above cited ROCK2 mRNA sequence are alternative splice forms, allelic forms, isozymes, or a cognate thereof. A cognate is a ROCK2 mRNA from another mammalian species that is homologous to SEQ ID NO:2 (an ortholog).

Attenuating expression of an mRNA: The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting one of the Rho kinase targets is administered to lower IOP. In other embodiments, two or more interfering RNAs targeting the same Rho kinase target (e.g., ROCK1) are administered to lower IOP. In still other embodiments, two or more interfering RNAs targeting both Rho kinase targets (e.g., ROCK1 and ROCK2) are administered to lower IOP.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of ROCK1 or ROCK2 may also be determined in vitro by evaluating target mRNA levels or target protein levels in, for example, human TM cells following transfection of ROCK1- or ROCK2-interfering RNA as described infra.

Inhibition of targets cited herein is also inferred in a human or mammal by observing an improvement in a glaucoma symptom such as improvement in intraocular pressure, improvement in visual field loss, or improvement in optic nerve head changes, for example.

Interfering RNA: In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, interfering RNA (e.g., siRNA) has a sense strand and an antisense strand, and the antisense strand comprises a region of at least near-perfect contiguous complementarity of at least 19 nucleotides to a target sequence of ROCK1 or ROCK2 mRNA, and the sense strand comprises a region of at least near-perfect contiguous identity of at least 19 nucleotides with a target sequence of ROCK1 or ROCK2 mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementary to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to a ROCK1 or ROCK2 target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA.

An embodiment of a 19-nucleotide DNA target sequence for ROCK1 mRNA is present at nucleotides 605 to 623 of SEQ ID NO:1:

```
5'-ATAACATGCTGCTGGATAA-3'.        SEQ ID NO: 3
```

An siRNA of the invention for targeting a corresponding mRNA sequence of SEQ ID NO:3 and having 21-nucleotide strands and a 2-nucleotide 3' overhang is:

```
5'-AUAACAUGCUGCUGGAUAANN-3'        SEQ ID NO: 4
3'-NNUAUUGUACGACGACCUAUU-5'.       SEQ ID NO: 5
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:3 and having 21-nucleotide strands and a 3'UU overhang on each strand is:

```
5'-AUAACAUGCUGCUGGAUAAUU-3'        SEQ ID NO: 6
3'-UUUAUUGUACGACGACCUAUU-5'.       SEQ ID NO: 7
```

The interfering RNA may also have a 5' overhang of nucleotides or it may have blunt ends. An siRNA of the invention for targeting a corresponding mRNA sequence of SEQ ID NO:3 and having 19-nucleotide strands and blunt ends is:

```
5'-AUAACAUGCUGCUGGAUAA-3'        SEQ ID NO: 80
3'-UAUUGUACGACGACCUAUU-5'.       SEQ ID NO: 81
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:2 and having a 19 bp double-stranded stem region and a 3'UU overhang is:

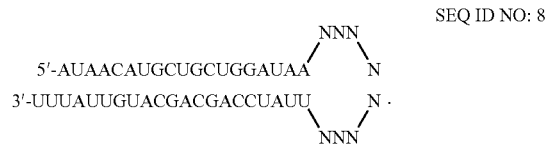

SEQ ID NO: 8

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:3) identified in the ROCK1 DNA sequence (SEQ ID NO:1) by 6 nucleotides yields a 25-nucleotide DNA target sequence present at nucleotides 605 to 629 of SEQ ID NO:1:

```
5'-ATAACATGCTGCTGGATAAATCTGG-3'.   SEQ ID NO: 82
```

A dicer-substrate 27-mer duplex of the invention for targeting a corresponding mRNA sequence of SEQ ID NO:82 is:

```
5'-AUAACAUGCUGCUGGAUAAAUCUGG-3'     SEQ ID NO: 83
3'-UUUAUUGUACGACGACCUAUUUAGACC-5'.  SEQ ID NO: 84
```

The two nucleotides at the 3' end of the sense strand (i.e., the GG nucleotides of SEQ ID NO:83) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of ROCK1 and ROCK2 DNA target sequences of SEQ ID NO:1 and SEQ ID NO:2, respectively, from which siRNAs of the present invention are designed in a manner as set forth above. ROCK1 and ROCK2 encode the two Rho kinase isoforms, as noted above.

TABLE 1

ROCK1 and ROCK2 Target Sequences for siRNAs

| ROCK1 Target Sequences | # of Starting Nucleotide with reference to SEQ ID NO: 1 | SEQ ID NO: |
|---|---|---|
| ATAACATGCTGCTGGATAA | 605 | 3 |
| GTACTTGTATGAAGATGAA | 653 | 9 |
| GTATGAAGATGAATAAGGA | 659 | 10 |
| TAGCTCCAATGCAGATAAA | 1248 | 11 |
| ATCAGTTGGAAGACTTAAA | 1562 | 12 |
| GACCTTCAAGCTCGAATTA | 1876 | 13 |
| GAACATTTGACTGGAAATA | 2266 | 14 |
| TAGCTCAGCTTACGAAACA | 2474 | 15 |
| ACGAAACAGTATAGAGGAA | 2485 | 16 |
| TTTGAATTGACGCAAGAAA | 2740 | 17 |
| CACTGTTAGTCGGCTTGAA | 2808 | 18 |
| ACAGCATGCTAACCAAAGA | 2834 | 19 |
| GTTAACAAATTGGCAGAAA | 3007 | 20 |
| ACCAGATGGTAGTGAAACA | 3146 | 21 |
| GTAGAAGAATGTGCACATA | 3199 | 22 |
| GCAAAGAGAGTGATATTGA | 3245 | 23 |
| GTACCAAATAGAGGAAATA | 3379 | 24 |
| GTTCTATAATGACGAACAA | 3453 | 25 |
| GATAAACTGTTTCACGTTA | 3511 | 26 |
| TAAACTGTTTCACGTTAGA | 3513 | 27 |
| GTTTCACGTTAGACCTGTA | 3519 | 28 |
| TGTCGAAGATGCCATGTTA | 3781 | 29 |
| GTCGAAGATGCCATGTTAA | 3782 | 30 |
| AACGACATCTCTTCTTCAA | 998 | 73 |
| GAAGAAACATTCCCTATTC | 1132 | 74 |
| TAGCAATCGTAGATACTTA | 1200 | 75 |
| GCCAATGACTTACTTAGGA | 1648 | 76 |
| GGACACAGCTGTAAGATTG | 1674 | 77 |
| GAGATGAGCAAGTCAATTA | 1708 | 78 |
| GTAACCAAAGCTCGTTTAA | 2077 | 79 |

TABLE 1-continued

ROCK1 and ROCK2 Target Sequences for siRNAs

| ROCK2 Target Sequences | #of Starting Nucleotide with reference to SEQ ID NO: 2 | SEQ ID NO: |
|---|---|---|
| ACAACATGCTCTTGGATAA | 1102 | 31 |
| TGTTAATACTCGCCTAGAA | 1865 | 32 |
| GAAAGCTGATCATGAAGCA | 2000 | 33 |
| CAGCTGGAATCTAACAATA | 2229 | 34 |
| GATATGACATACCAACTAA | 2514 | 35 |
| AGGCACGACTAGCAGATAA | 2584 | 36 |
| ATTAGACTGTGACCTCAAA | 2738 | 37 |
| GATGATGGCTAGACACAAA | 3305 | 38 |
| CTAAAGAAATTCCAAGGAT | 4111 | 39 |
| TCGTATTCTTCCAGTGAAA | 4652 | 40 |
| TTGCAACTATGCACTTGTA | 5184 | 41 |
| CAACTATGCACTTGTATAA | 5187 | 42 |
| GTTGCATGTTCATGTTTAA | 5255 | 43 |
| TTCCTAATGCTTCATGATA | 5315 | 44 |
| CTAGCTTTGTGGAAGATAA | 5439 | 45 |
| GAAGATAAATCGTGCACTA | 5450 | 46 |
| CCTTGATGTCTGTCTATTA | 5578 | 47 |
| CTTGATGTCTGTCTATTAT | 5579 | 48 |
| TTTACAGACCTCAGTATTA | 5611 | 49 |
| TATTAGTCTGTGACTACAA | 5625 | 50 |
| TAAATATGATCCTCAGACA | 5795 | 51 |
| CAGCAATGGTAAGCGTAAA | 6000 | 52 |
| CTCCGTCTCTACCAATATA | 6228 | 53 |
| TGATGGTGGTGGCCTGTAA | 6264 | 54 |
| CTTGCTGGATGGCTTAAAT | 584 | 55 |
| GGATTCACTTGTAGGAACA | 1337 | 56 |
| TCATCGGATTACCTACTA | 1678 | 57 |
| TAAATGAGCTCCTTAAACA | 2773 | 58 |
| GTTAGAAACCTGACATTAA | 2814 | 59 |
| ATAACCATCTCATGGAAAT | 2941 | 60 |
| TCTCTTGAGGAAACTAATA | 3357 | 61 |
| CAATCTTGCAAATGAGAAA | 3398 | 62 |
| TAAGCGCAGCAGCTATTAA | 3481 | 63 |
| GAGAATAGAAAGCTACATA | 3633 | 64 |
| GCTACATATGGAGCTTAAA | 3644 | 65 |
| CTACATATGGAGCTTAAAT | 3645 | 66 |
| GATGACATTGGACAGTAAA | 3767 | 67 |

TABLE 1-continued

ROCK1 and ROCK2 Target Sequences for siRNAs

| TCTGGATAGTTCCAGTATA | 3836 | 68 |
| GAACAATCCAATCCTTACA | 4023 | 69 |
| GTATAGAGCAGATGCTAAA | 4097 | 70 |
| ATAAAGCCATAATGTTGGA | 5202 | 71 |
| TAGCTTTGTGGAAGATAAA | 5440 | 72 |

As cited in the examples above, one of skill in the art is able to use the target sequence information provided in Table 1 to design interfering RNAs having a length shorter or longer than the sequences provided in the table and by referring to the sequence position in SEQ ID NO:1 or SEQ ID NO:2 and adding or deleting nucleotides complementary or near complementary to SEQ ID NO:1 or SEQ ID NO:2 respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

The target sequence in the mRNAs corresponding to SEQ ID NO:1 or SEQ ID NO:2 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1 or SEQ ID NO:2. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Minis, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization under Physiological Conditions: In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m° C.=81.5+16.6(\log_{10}[Na+])+0.41$ (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-stranded interfering RNA: As cited above, interfering RNAs ultimately function as single strands. Single-stranded (ss) interfering RNA has been found to effect mRNA silencing, albeit less efficiently than double-stranded siRNA. Therefore, embodiments of the present invention also provide for administration of a ss interfering RNA that hybridizes under physiological conditions to a portion of SEQ ID NO:1 or SEQ ID NO:2 and has a region of at least near-perfect contiguous complementarity of at least 19 nucleotides with the hybridizing portion of SEQ ID NO:1 or SEQ ID NO:2, respectively. The ss interfering RNA has a length of 19 to 49 nucleotides as for the ds siRNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin interfering RNA: A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of administration: Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

Interfering RNA may be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Subject: A subject in need of treatment for ocular hypertension or at risk for developing ocular hypertension is a human or other mammal having ocular hypertension or at risk of having ocular hypertension associated with undesired or inappropriate expression or activity of targets as cited herein, i.e., ROCK1 or ROCK2. Ocular structures associated with such disorders may include the eye, retina, choroid, lens, cornea, trabecular meshwork, iris, optic nerve, optic nerve head, sclera, anterior or posterior segments, or ciliary body, for example. A subject may also be an ocular cell, cell culture, organ or an ex vivo organ or tissue.

Formulations and Dosage: Pharmaceutical formulations comprise interfering RNAs, or salts thereof, of the invention up to 99% by weight mixed with a physiologically acceptable carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

|  | Amount in weight % |
| --- | --- |
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

|  | Amount in weight % |
| --- | --- |
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
| --- | --- |
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

|  | Amount in weight % |
| --- | --- |
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNAs of embodiments of the invention results in an extracellular concentration at the surface of the target cell of from 100 pM to 1 μM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the target organ one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with interfering RNAs directed against ROCK1 or ROCK2 mRNA is expected to be beneficial over small molecule treatments by increasing the duration of action, thereby allowing less frequent dosing and greater patient compliance.

An effective amount of a formulation may depend on factors such as the age, race, and sex of the subject, the severity of the ocular hypertension, the rate of target gene transcript/protein turnover, the interfering RNA potency, and the interfering RNA stability, for example. In one embodiment, the interfering RNA is delivered topically to a target organ and reaches the ROCK1 or ROCK2 mRNA-containing tissue such as the trabecular meshwork, retina or optic nerve head at a therapeutic dose thereby ameliorating an ocular hypertension-associated disease process.

Acceptable carriers: An acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Mirus Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits: Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also contains a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of interfering RNA to knock-down the levels of endogenous target gene expression in, for example, human trabecular meshwork (TM) cells is evaluated in vitro as follows. Transformed human TM cells, for example, cell lines designated GTM-3 or HTM-3 (see Pang, I. H. et al., 1994. *Curr. Eye Res.* 13:51-63), are plated 24 h prior to transfection in standard growth medium (e.g., DMEM supplemented with 10% fetal bovine serum). Transfection is performed using Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROLT™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, TAQMAN® forward and reverse primers and a probe set that preferably encompasses the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in TM cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression.

The ability of interfering RNAs of the present invention to knock-down levels of Rho kinase protein expression is further exemplified in Examples 1 and 2 as follows.

Example 1

Interfering RNA for Specifically Silencing ROCK1 in Trabecular Meshwork Cells

The present study examines the ability of ROCK1-interfering RNA to knock down the levels of endogenous ROCK1 expression in cultured human glaucomatous trabecular meshwork (TM) cells.

Transfection of GTM-3 cells (Pang, I. H., et al., 1994 *Curr Eye Res.* 13:51-63) was accomplished using standard in vitro concentrations (100 nM) of ROCK1 or ROCK2 siRNAs, or a non-targeting control siRNA and DHARMAFECT® #1 transfection reagent (Dharmacon, Chicago, Ill.). All siRNAs were dissolved in 1× siRNA buffer, an aqueous solution of 20 mM KCl, 6 mM HEPES (pH 7.5), 0.2 mM $MgCl_2$. ROCK1 protein expression was evaluated by western blot analysis 72 hours post-transfection. The ROCK1 siRNAs are double-stranded interfering RNAs having specificity for the following targets: siROCK1#1 targets SEQ ID NO:23; siROCK1#2 targets SEQ ID NO:29; siROCK1#3 targets SEQ ID NO:10; siROCK1#4 targets SEQ ID NO:9. The siROCK2 sequences are set forth in Example 2, infra. At 100 nM, each of the four ROCK1 siRNAs decreased ROCK1 expression relative to a non-targeting control siRNA as shown by the western blot data of FIG. 1. SiROCK1#2 targeting SEQ ID NO:29 and siROCK1#3 targeting SEQ ID NO:10 appeared to be particularly effective. The ROCK2 siRNAs had little, if any, effect on ROCK1 expression, confirming the specificity of ROCK2 siRNAs for the ROCK2 target.

Figure 2:
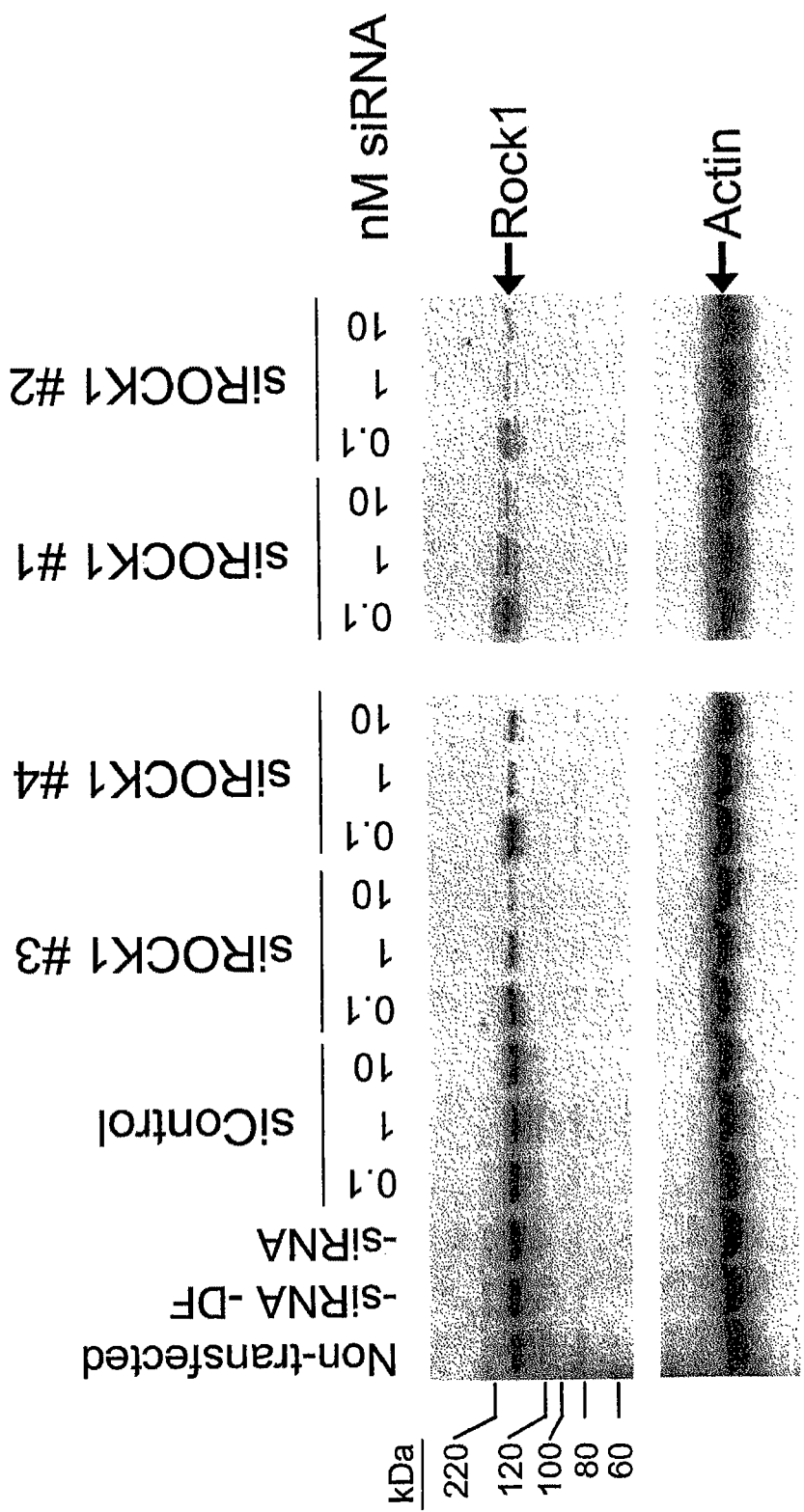
FIG. 2 provides a ROCK1 western blot of GTM-3 cells transfected with ROCK1 siRNAs #1, #2, #3, and #4, and a non-targeting control siRNA, each at 10 nM, 1 nM, and 0.1 nM, and a buffer control (-siRNA). The arrows indicate the positions of the 160-kDa ROCK1 protein and the 42-kDa actin protein bands.

A further study was carried out using the siRNAs at lower concentrations. GTM-3 cells were transfected with the ROCK1 or non-targeting control siRNAs at 10 nM, 1 nM, and 0.1 nM, and target gene expression was evaluated by western blot analysis 72 hours post-transfection. Control samples included a buffer control in which the volume of siRNA was replaced with an equal volume of 1× siRNA buffer (-siRNA). As shown by the data of FIG. 2, each of the four ROCK1 siRNAs reduced ROCK1 protein expression significantly at 10 nM and 1 nM, however, siROCK1#2 also silenced ROCK1 protein expression relatively effectively at 0.1 nM.

Example 2

Interfering RNA for Specifically Silencing ROCK2 in Trabecular Meshwork Cells

The present study examines the ability of ROCK2-interfering RNA to knock down the levels of endogenous ROCK2 expression in cultured human glaucomatous trabecular meshwork (TM) cells.

Figure 3:
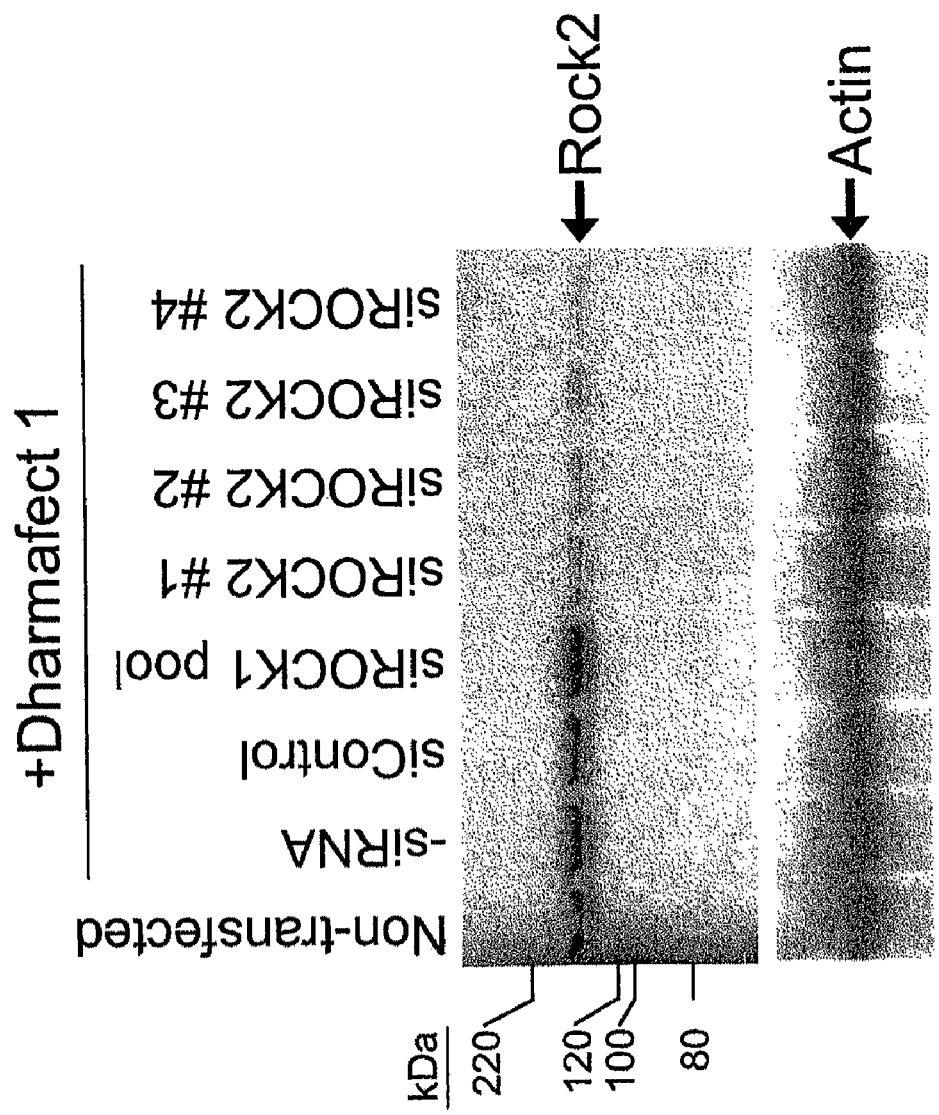
FIG. 3 provides a ROCK2 western blot of GTM-3 cells transfected with ROCK2 siRNAs #1, #2, #3, and #4, a ROCK1 pool, and a non-targeting control siRNA, each at 100 nM, and a buffer control (-siRNA). The arrows indicate the positions of the 160-kDa ROCK2 protein and the 42-kDa actin protein bands.

Transfection of GTM-3 cells (Pang, I. H., et al., 1994 *Curr Eye Res.* 13:51-63) was accomplished using standard in vitro concentrations (100 nM) of ROCK1 or ROCK2 siRNA, or a non-targeting control siRNA and DHARMAFECT® #1 transfection reagent (Dharmacon, Chicago, Ill.). ROCK2 protein expression was evaluated by western blot analysis 72 hours post-transfection. The ROCK2 siRNAs are double-stranded interfering RNAs having specificity for the following targets: siROCK2#1 targets SEQ ID NO:33; siROCK2#2 targets SEQ ID NO:38; siROCK2#3 targets SEQ ID NO:34; siROCK2#4 targets SEQ ID NO:39. At 100 nM, each of the four ROCK2 siRNAs decreased ROCK2 expression relative to a non-targeting control siRNA and relative to a pool of ROCK1-specific siRNAs as shown by the western blot data of FIG. 3. The ROCK1 siRNA pool had little, if any, effect on ROCK2 expression, confirming the specificity of ROCK1 siRNAs for the ROCK1 target.

Figure 4:
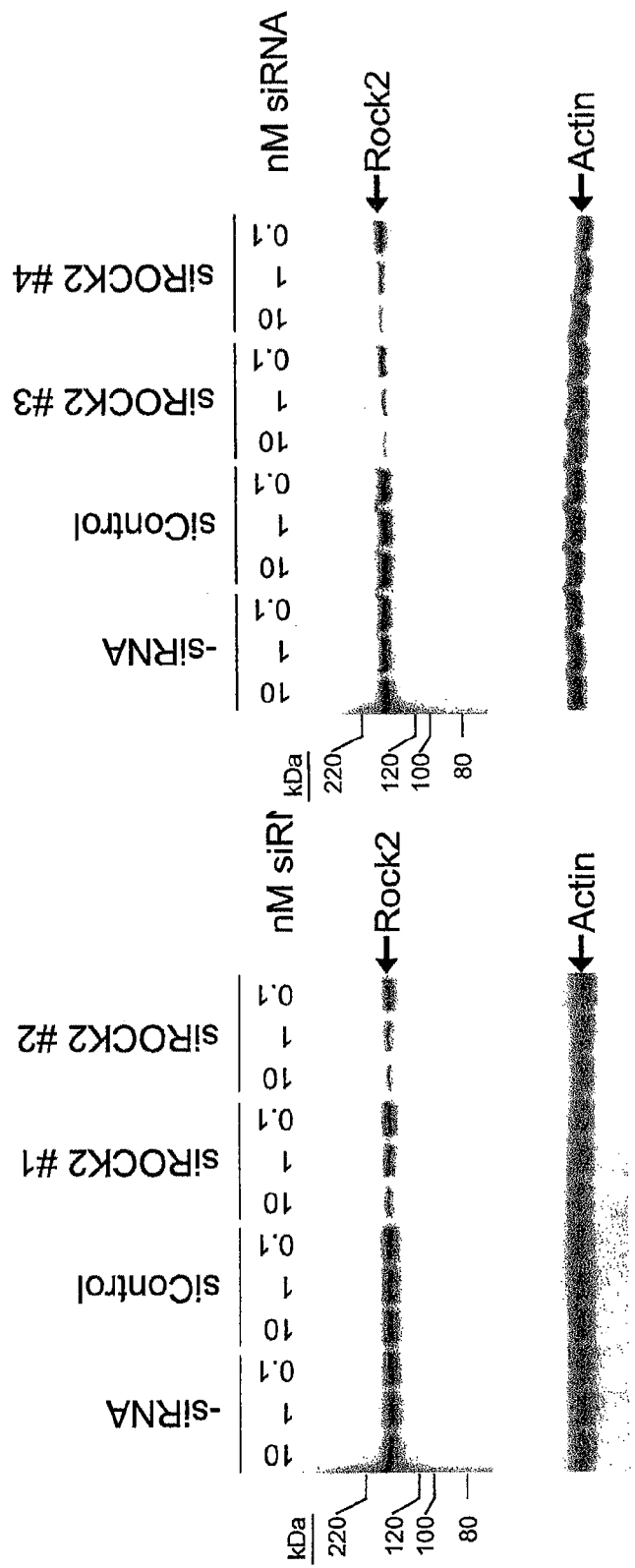
FIG. 4 provides a ROCK2 western blot of GTM-3 cells transfected with ROCK2 siRNAs #1, #2, #3, and #4, and a non-targeting control siRNA, each at 10 nM, 1 nM, and 0.1 nM, and a buffer control (-siRNA). The arrows indicate the positions of the 160-kDa ROCK2 protein and the 42-kDa actin protein bands.

A further study was carried out using the siRNAs at lower concentrations. GTM-3 cells were transfected with the ROCK2 or non-targeting control siRNAs at 10 nM, 1 nM, and 0.1 nM, and target gene expression was evaluated by western blot analysis 72 hours post-transfection. Control samples included a buffer control in which the volume of siRNA was replaced with an equal volume of 1× siRNA buffer (-siRNA). As shown by the data of FIG. 4, each of the four siRNAs reduced ROCK2 protein expression significantly at 10 and 1 nM, with siROCK2#3 exhibiting slightly greater efficacy than the others.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A method of attenuating expression of Rho kinase mRNA of a subject, comprising:
    administering to an eye of the subject a composition comprising an effective amount of interfering RNA having a length of 19 to 49 nucleotides and a pharmaceutically acceptable carrier, the interfering RNA comprising:
        a sense nucleotide strand and an antisense nucleotide strand wherein the antisense strand:
            comprises a ribonucleotide sequence consisting of the base sequence of SEQ ID NO: 26 with uridine bases substituted for thymidine bases; and
            is substantially complementary to the sense strand;
        wherein the interfering RNA directs RISC-mediated cleavage of Rho kinase mRNA, and wherein the expression of Rho kinase mRNA is attenuated thereby.

2. The method of claim 1 wherein the subject is a human and the human has ocular hypertension.

3. The method of claim 1 wherein the subject is a human and the human has glaucoma.

4. The method of claim 1 wherein the composition is administered via a topical, intravitreal, transcleral, periocular, conjunctival, subtenon, intracameral, subretinal, subconjunctival, retrobulbar, or intracanalicular route.

5. The method of claim 1 wherein the antisense strand is designed to target an mRNA corresponding to a portion of SEQ ID NO:1 that is 19 to 49 nucleotides in length and begins at nucleotide.

6. The method of claim 1 wherein the sense nucleotide strand and the antisense nucleotide strand are connected by a hairpin loop.

7. A method of attenuating expression of Rho kinase mRNA of a subject, comprising:
    administering to an eye of the subject a composition comprising an effective amount of single-stranded interfering RNA having a length of 19 to 49 nucleotides and a pharmaceutically acceptable carrier,
        wherein the single-stranded interfering RNA hybridizes under physiological conditions to a portion of mRNA corresponding to SEQ ID NO:1 beginning at nucleotide 3511, and the interfering RNA has a region of at least 80% to 100 contiguous complementarity of at least 19 nucleotides with the hybridizing portion of mRNA that is 19 to 49 nucleotides in length and corresponds to a portion of SEQ ID NO: 1 that begins at nucleotide 3511,
    wherein the interfering RNA directs cleavage of Rho kinase mRNA, and wherein the expression of Rho kinase mRNA is thereby attenuated.

8. A method of attenuating expression of Rho kinase mRNA in a subject, the method comprising:
    administering to an eye of the subject a composition comprising an effective amount of interfering RNA having a length of 19 to 49 nucleotides and a pharmaceutically acceptable carrier, the interfering RNA comprising:
        a region of at least 13 contiguous nucleotides having at least 90% sequence complementarity to, or at least 90% sequence identity with, the penultimate 13 nucleotides of the 3' end of a ribonucleotide sequence consisting of the base sequence of SEQ ID NO: 26, with uridine bases substituted for thymidine bases
    wherein the interfering RNA directs RISC-mediated cleavage of Rho kinase mRNA, and wherein the expression of the Rho kinase mRNA is attenuated thereby.

9. The method of claim 8 wherein the Rho kinase mRNA is ROCK1 mRNA and the interfering RNA comprises:
    a region of at least 13 contiguous nucleotides having at least 90% sequence complementarity to, or at least 90% sequence identity with, the penultimate 13 nucleotides of the 3' end of an mRNA corresponding to SEQ ID NO: 26.

10. The method of claim 8 wherein the interfering RNA comprises a region of at least 14 contiguous nucleotides having at least 85% sequence complementarity to, or at least 85% sequence identity with, the penultimate 14 nucleotides of the 3' end of an mRNA corresponding to the sequence identified by the sequence identifier.

11. The method of claim 8 wherein the interfering RNA comprises a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to the sequence identified by the sequence identifier.

12. The method of claim 8, wherein the subject has ocular hypertension.

13. The method of claim 8, wherein the subject has glaucoma.

14. The method of claim 8 wherein the composition is administered via a topical, intravitreal, transcleral, periocular, conjunctival, subtenon, intracameral, subretinal, subconjunctival, retrobulbar, or intracanalicular route.

15. The method of claim 8 wherein the composition is administered via in vivo expression from an interfering RNA expression vector.

* * * * *